United States Patent [19]

Karlsson

[11] 4,126,491

[45] Nov. 21, 1978

[54] METHOD AND APPARATUS FOR PRODUCING METAL BLANKS, IN PARTICULAR STEEL SLABS, WHICH AT LEAST IN A PREDETERMINED SURFACE AREA HAVE SUBSTANTIALLY NO DEFECTS

[75] Inventor: Per-Olle Karlsson, Oxelösund, Sweden

[73] Assignee: Gränges Oxelösund Järnverk AB, Sweden

[21] Appl. No.: 591,937

[22] Filed: Jun. 30, 1975

[30] Foreign Application Priority Data

Jun. 28, 1974 [DE] Fed. Rep. of Germany ....... 2431173

[51] Int. Cl.² .......................... B23K 7/06; B23K 7/10
[52] U.S. Cl. ...................................... 148/9.5; 266/51; 324/238; 324/240
[58] Field of Search ................ 148/9.5; 266/23 H, 51; 90/13 R; 51/165.71; 324/37

[56] References Cited

U.S. PATENT DOCUMENTS

| | | | |
|---|---|---|---|
| 3,020,033 | 2/1962 | McCreanor et al. | 148/9.5 |
| 3,216,867 | 11/1965 | De Vries et al. | 148/9.5 |
| 3,245,842 | 4/1966 | Miller et al. | 148/9.5 |
| 3,593,120 | 7/1971 | Mandula, Jr. | 324/37 |
| 3,609,531 | 9/1971 | Forster | 324/37 |
| 3,633,010 | 1/1972 | Svetlichny | 148/9.5 |
| 3,657,638 | 4/1972 | Höller et al. | 324/37 |
| 3,676,959 | 7/1972 | Forster | 324/37 |
| 3,676,960 | 7/1972 | Aspden | 51/165.71 |
| 3,822,632 | 7/1974 | Chigiotti | 148/9.5 |
| 3,822,632 | 7/1974 | Chigiotti | 144/2 M |
| 3,906,677 | 9/1975 | Gunter et al. | 51/165.71 |
| 3,967,193 | 6/1976 | Bergstrand | 324/37 |

*Primary Examiner*—W. Stallard
*Attorney, Agent, or Firm*—Craig & Antonelli

[57] ABSTRACT

Method and apparatus for producing metal blanks, in particular steel slabs, which at least in a predetermined surface area have substantially no defects such as cracks, seams, bubbles, scabs, or the like, at least the surface portion to be made free of defects being systematically and substantially completely scanned by means of at least one inspecting device which detects such defects at and closely beneath the surface as regards location and depth and a working means being controlled by means of the recorded defects, which by scarfing, grinding, milling, planing and/or another cutting machine and/or local material melt deposition and/or material replacement or the like removes the defects detected, the defects being recorded with their depth for surface sub-areas whose width transversely of the working means is substantially equal or less than the smallest working width of the working means and the working depth of the working means being controlled in accordance with the maximum defect depth recorded for the particular surface sub-area to be worked.

39 Claims, 5 Drawing Figures

METHOD AND APPARATUS FOR PRODUCING METAL BLANKS, IN PARTICULAR STEEL SLABS, WHICH AT LEAST IN A PREDETERMINED SURFACE AREA HAVE SUBSTANTIALLY NO DEFECTS

The invention relates to a method and apparatus for producing metal blanks, in particular steel slabs, which at least in a predetermined surface area have substantially no defects such as cracks, seams, bubbles, scabs or the like, such defects being detected at least in the defect-free surface area to be produced and where necessary removed by a machining means by scarfing, grinding, milling, planing and/or another cutting machining and/or local material melting deposition and/or material replacement.

According to the conventional present-day method of making sheet metal blanks, so-called slabs, are processed which originate in some cases from billets cast in moulds and in some cases from continuously cast material. On the surface of these slabs or in the vicinity of this surface defects are found in the form of cracks, bubbles, scabs and the like. After the further processing of these slabs, which usually consists of heating to the working temperature and rolling to sheet or flat steel, these defects, in a somewhat changed form, are present on the sheet surface unless they are removed prior to the further processing.

The possiblities of detecting all these defects in the slab state are today considered very unreliable because the defect testing is done with the aid of ocular inspection. The defects found have been characterized in the visual inspection by ink or other means. In particular, it is not possible with this known testing method to assess the depth variation of the defects, i.e. three-dimensionally. As a result, slabs which because of deep defects are to be considered rejections, are further processed. The removal of the defects can be effected by means of oxygen scarfing, planing, milling or another surface treatment method. Of these methods, manual oxygen scarfing is the one most frequently used today but it is also the method which requires the most physical work from the ergonomical point of view. In recent time there has been a certain trend to manually operated scarfing machines which are guided by hand to the defects on the slabs, employing manoeuvering units or systems know per se.

The problem underlying the present invention is to provide a method and an apparatus which permit a reliable detection of the aforementioned defects on and closely beneath the surface of blanks, in particular slabs, and facilitate the difficult manual work in removing the defects by means of oxygen scarfing or the like.

This problem is solved according to the invention in that at least one inspecting device is employed which detects such defects at and closely beneath the surface as regards location and depth and the defects for surface portions whose width transversely of the working or machining means is substantially equal to or less than the smallest working width of the working means are recorded with their depths and that the working depth of the working means is controlled in accordance with the maximum defect depth recorded for the particular surface portion to be worked.

Apart from obviating the hitherto manual operation, which is particularly valuable from the health point of view, the method according to the invention has the advantage that with sheet metal produced according to the method of the invention only about 5% of the finished sheets have minor defects whereas about 35% of the sheets which are tested, scarfed and finish-rolled according to the known method described at the beginning have major defects.

According to the invention it is particularly advantageous to record the defects divided according to their depth into a plurality of depth classes and to control or select the working depth and/or type of working in dependence upon the recorded depth classes of the defects. It may also be very advantageous for technical-economic reasons to select the type of working for in each case one of the slab surfaces or for both slab surfaces in dependence upon the defect depth recorded for said services and preferably also in dependence upon the number of the defects recorded in the individual depth classes for these surfaces in order to choose the optimum type of working or machining corresponding to the different defect depth and the different number of defects of the individual slabs or the individual slab surfaces. According to the invention, it is possible when a defect is recorded whose depth goes beyond a predetermined maximum depth to separate the particular slab out as scrap without further processing. From the technical-economical point of view this elimination of such slabs is particularly important. According to the invention, expediently slabs in which at least in the surface area to be made free of defects no defects are recorded or only defects not beyond a predetermined small depth are separated out as faultless.

According to the invention at least the surface portions of the slab to be made free of defects are divided by means of a preferably right-angle coordinate system into sub-areas whose width is substantially equal to or a fraction of the smallest working width of the working or machining means and by means of the inspecting means in each of the sub-areas thus defined at least the maximum defect depth is detected and preferably correspondingly to a predetermined defect depth classification for each sub-area the depth class is recorded under which the maximum defect depth of the respective sub-area detected by means of the inspecting means falls in such a manner that the values thus recorded represent a three-dimensional approximation to the actual depth path of the defects, the extension of the individual surface sub-areas in the direction of the relative feed between the working means and the slab expediently being made substantially equal to or smaller than the width of the surface sub-areas.

With the method according to the invention a slab to be inspected may be brought into a predetermined position at an inspection station and whilst held substantially unchanged in said position scanned by at least one inspecting means at least in the surface portion to be made free of defects corresponding to a strip system which is defined by a predetermined coordinate system and the working of the surface region to be made free of defects thus inspected carried out by the working means either in the same position of the slab at the inspection station or after conveying the slab to a special working station in a position corresponding substantially exactly to its position at the inspection station on the basis of the same coordinate system. On conveying the slabs to a special working station it may be expedient to mark the position of the slab, in particular the zero point and/or the direction of the coordinate system, on the slabs.

According to the invention a working or machining means whose working width is equal to the inspecting width of the inspecting means may be led behind the inspecting means over the slab surface, which is controlled directly by the inspecting means with a time delay corresponding to the distance between the two means, which has the advantage that it is not necessary to realign the position of the slab for working, and the inspecting and working means may have a smaller width than the slab.

It may be advantageous by means of a marking device — in particular an ink or colour marking device — which is preferably coupled to the inspecting means and preferably controlled automatically by the latter to mark the defects and/or individual or all coordinate lines and/or the zero point of the coordinate system.

In a preferred modification of the method according to the invention the defects registered by location and depth are stored on a data carrier and the machining or working means controlled by means of said data carrier, e.g. magnetic tape, magnetic record, punched tape, punched card, or the like.

According to the invention, generally the one surface of the slabs is first scanned by an inspecting means and thereafter the slab is turned and the other surface of the slab scanned by the same detecting means or by a similar second means. After the inspection of both slab surfaces the slabs classified as faultless and those classified as scrap can be separated out and the slabs to be worked fed to a working means or distributed to a plurality of working means of the same or different type, it being possible to combine at least some of the working means via a slab-turning means with another working means to achieve successive working of the two flat sides of the slab and a uniform capacity utilization of the individual working means by suitable distribution of the slabs to the working means.

Advantageously, the inspecting means are of the type which detect the defects and the particular defect depth substantially independently of their movement or scan direction relatively to a longitudinal extent of a defect, the slab surface being scanned by means of one or more of such inspecting means in strip manner with a strip width corresponding to the inspecting width of an inspecting means in such a manner that the strips substantially completely cover the slab surface substantially without gaps or overlapping at least in their edge regions. Preferably, the slab surface is scanned in parallel strips transversely of the rolling direction, which has the advantage that the surface undulations originating from the rolling operation and extending parallel to the rolling direction and thus primarily longitudinally of the slab do not appreciably falsify the result of the measurement.

If the slab surface is to be inspected by means of one or more inspecting means which detect the defect depth and supply a result which is appreciably dependent on the movement or scanning direction thereof relatively to a longitudinal extent of a defect, the slab surface can be scanned in a strip manner with a strip width corresponding to the inspection width of an inspecting means in two groups of strips intersecting each other at an angle of preferably 90° in such a manner that the strips of each group substantially completely cover the slab surface substantially without gaps or overlapping at their edges.

Preferably, the slab surface is scanned on a predetermined x-y coordinate system by means of at least one inspecting means at least parallel to one coordinate direction and in each individual sub-area defined by two adjacent x and y coordinate lines the deepest defect detected by the inspecting means in said sub-area is recorded in its depth.

According to the invention the x-y coordinate system may be disposed parallel to the longitudinal and transverse direction of the slabs with its zero point in a corner of the slab surface to be inspected.

According to the invention at least the slab surface to be made free of defects is scanned in strip manner by means of inspecting heads disposed on a support arm preferably in a line adjacent each other, the distance between the scanned strips of two adjacent inspecting heads being equal to a strip width or equal to an integral multiple of a strip width. In this case the support arm with the inspecting means is displaced perpendicularly to the strips by 1, 2, 3, etc. strip widths after each scanning of the slab surface and said surface then scanned in the same or in the opposite direction until there are no unscanned fields between the scanned strips.

Preferably, the length of the holding arm for the inspecting heads is made equal to a fraction of a maximum possible extension of the slab surface to be inspected.

According to the invention each inspecting means in particular each inspecting head is individually mounted in particular on a support arm is such a manner that on scanning the slab surface they remain constantly and preferably slidingly in engagement on the slab surface or maintain constantly a constant distance from said surface and move exactly in the scanning direction without lateral displacement or deviation so that inaccurate or erroneous indications are avoided. The inspecting heads may be mounted movably in the direction perpendicular to the slab surface and under biasing preferably by means of a spring or of a hydraulic piston pressed against the slab surface preferably with a predetermined force.

The scanning is preferably carried out with the slab stationary. This has the advantage that the scan width of the inspecting means may be substantially smaller than the slab width if by means of one or more inspecting means firstly a strip of the slab surface is scanned in a predetermined direction and thereafter substantially in the same scan direction further strips of the slab surface not scanned in the first scanning are scanned until the slab surface has been substantially completely scanned. According to the invention the machining or working of the slab surface may also be undertaken with the slab stationary in that the working means whose working width is equal to or equal to a multiple of the scanning width of the inspecting means is led in analogous manner over the sub-areas of the slab surface in which defects have been recorded.

Alternatively, the inspecting means or plurality of inspecting means and/or the working means may be disposed on a base support which is moved with the same velocity and in the same direction as the slab to be inspected in such a manner that there is no relative movement between said base support and the slab and the actual inspecting means and the working means led in a manner analogous to the case of a stationary slab over the slab surface, the actual working means executing relatively to the base supports the same movements as in the case of a stationary slab.

For detecting defects all measuring techniques which make it possible to measure the position and depth extension relative to the slab surface of irregularities and defects, in particular cracks, bubbles, scabs, seams or the like, are suitable. In particular, the known eddy-current techniques may be used as may be the known magnetic leakage or stray flux techniques in which the magnetic stray field is sensed and measured by means of probes, such as surface-wave probes, magnet-sensitive semiconductors, induction coils or the like, preferably in differential circuit connection, or is recorded by means of a magnetic tape brought onto the slab surface to be inspected.

An inspection for defects can alternatively be carried out according to the invention by means of ultrasonic or X-rays or by means of electrical resistance measurements. With all these measuring techniques it may be expedient to carry out two measurements in succession in order for example to reliably detect elongated cracks independently of the scanning direction of the inspecting means. For this purpose the two measurements are generally carried out at an angle of 90° to each other. This may also be done by using for example in the case of magnetic stray flux measurements an inspecting head which by means of a first magnetization device effects a magnetization at an angle of 45° to the scanning direction, by means of one or more first probe or coil pairs preferably in differential connection the magnetic stray field is measured, and by means of a second magnetization device disposed at a distance from the first magnetization is effected perpendicular to the first magnetization and the stray field thereof is also measured by probe pairs, the signals obtained on the basis of the two magnetizations being combined to determine the maximum defect depth.

It may also be advantageous to scan the surface to be inspected by means of oscillating probes or probe pairs, which is particularly advantageous if as in the case of stray flux probes the probes effect a substantially punctiform scanning. In this case the probes then describe on the surface to be inspected a narrow zig-zag or sinusoidal curve group.

The inventon will be explained in detail hereinafter with the aid of schematic drawings of an example of embodiment.

In the drawings,

FIG. 1 is a perspective illustration of a slab whose upper flat side is divided by means of an x-y coordinate system into 72 sub-areas or elemental areas, the zero point N of the coordinate system lying in a corner of the slab.

Figure 1:
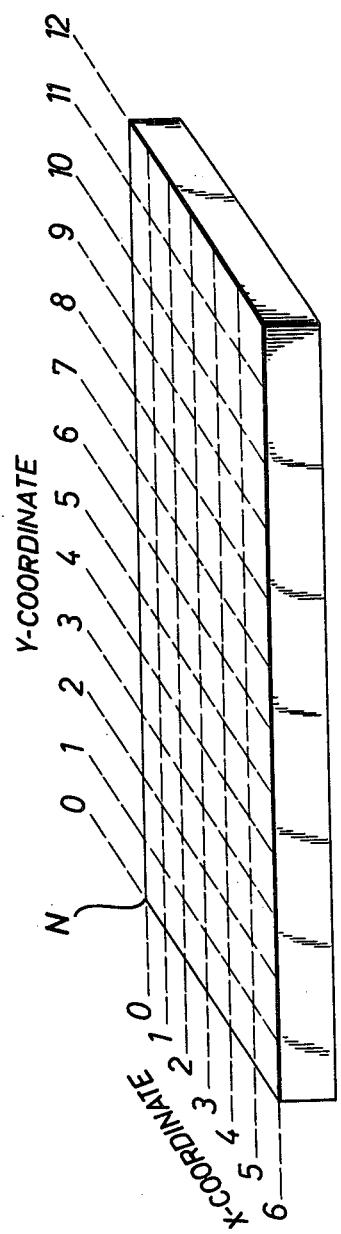
FIG. 1 shows a perspective view of a slab whose flat side is divided by means of an x-y coordinate system into sub-areas.
Figure 2:
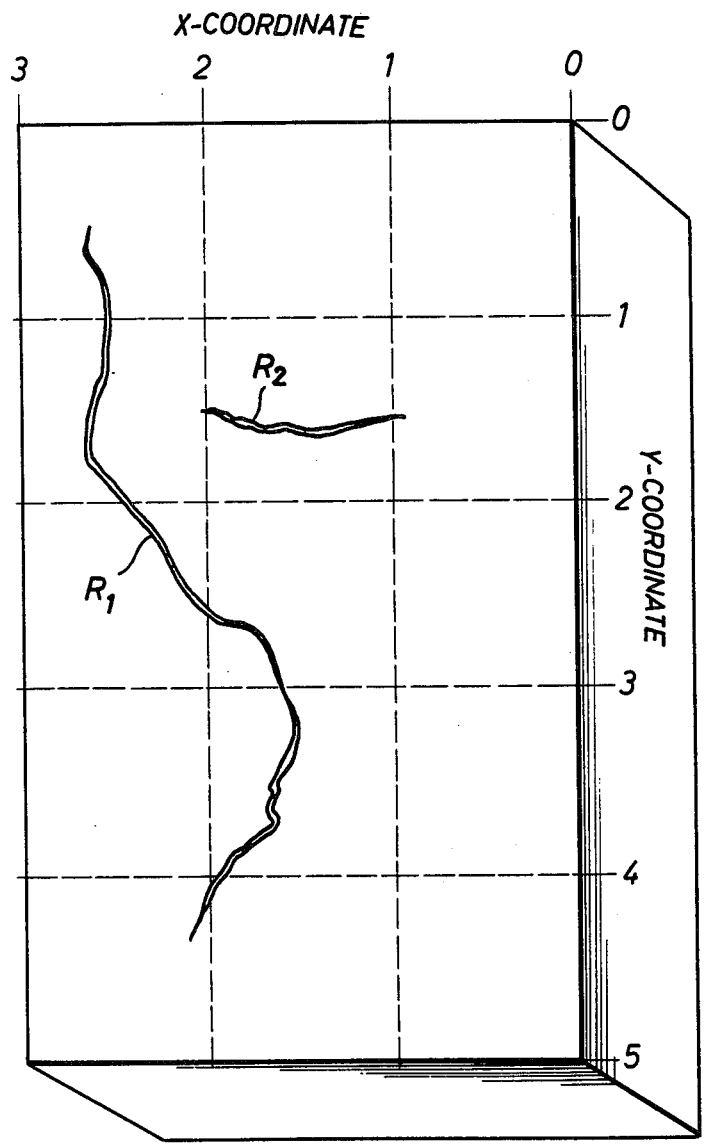
FIG. 2 shows a fragment of the slab according to FIG. 1 to an enlarged scale.
Figure 2A:
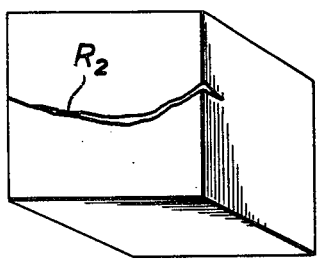
FIG. 2a is a perspective illustration of a sub-area.
Figure 2B:
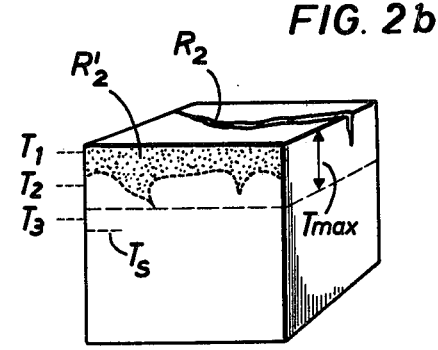
FIG. 2b shows the sub-area of FIG. 2a from the front.

FIG. 2 shows to an enlarged scale a fragment of the slab according to FIG. 1 comprising 15 sub-areas, two cracks $R_1$ and $R_2$ being indicated. The sub-area comprising the crack $R_2$ and disposed between the x coordinates 1 and 2 and the y coordinates 1 and 2 is illustrated separately in FIG. 2a. In FIG. 2b the depth path and the maximum depth $T_{max}$ of the crack $R_2$ are apparent from the projection $R_2'$ thereof. $T_1$ is the maximum depth to which surface defects may penetrate the slabs without having a detrimental effect on the quality of the sheet metal. Such defects need therefore not be removed. In practice, $T_1$ is about 2–3 mm. In FIG. 2b $T_2$ and $T_3$ define the limit of the depth classes, defects having a depth between $T_1$ and $T_2$ being removed with a working depth $T_2$ and defects having a depth between $T_2$ and $T_3$ with a working depth of $T_3$. $T_s$ is the defect depth which when exceeded means that the slabs are to be separated out as scrap. $T_s$ depends on the slab thickness and is generally about ⅓ of said thickness but not more than about 25–30 mm. The scanning of the slab surface may for example be effected with an inspecting means having three inspecting heads, each of which has a scanning width of one y coordinate unit, said heads being arranged on a support arm a distance apart which is such that between them in each case a strip of one y coordinate unit is not scanned. With such an inspecting means, during a first movement transversely of the slab, i.e. parallel to the x axis, the strips between the y coordinate lines 0 and 1 as well as between 2 and 3 and between 4 and 5 are scanned; thereafter, after lateral displacement of the inspecting means through one y unit the strips between the y coordinates 1 and 2 and 3 and 4 as well as 5 and 6 are scanned during a second movement transversely of the slab. After a lateral displacement of the inspecting means through five y units to the right the right slab half may be scanned analogously.

Figure 3:
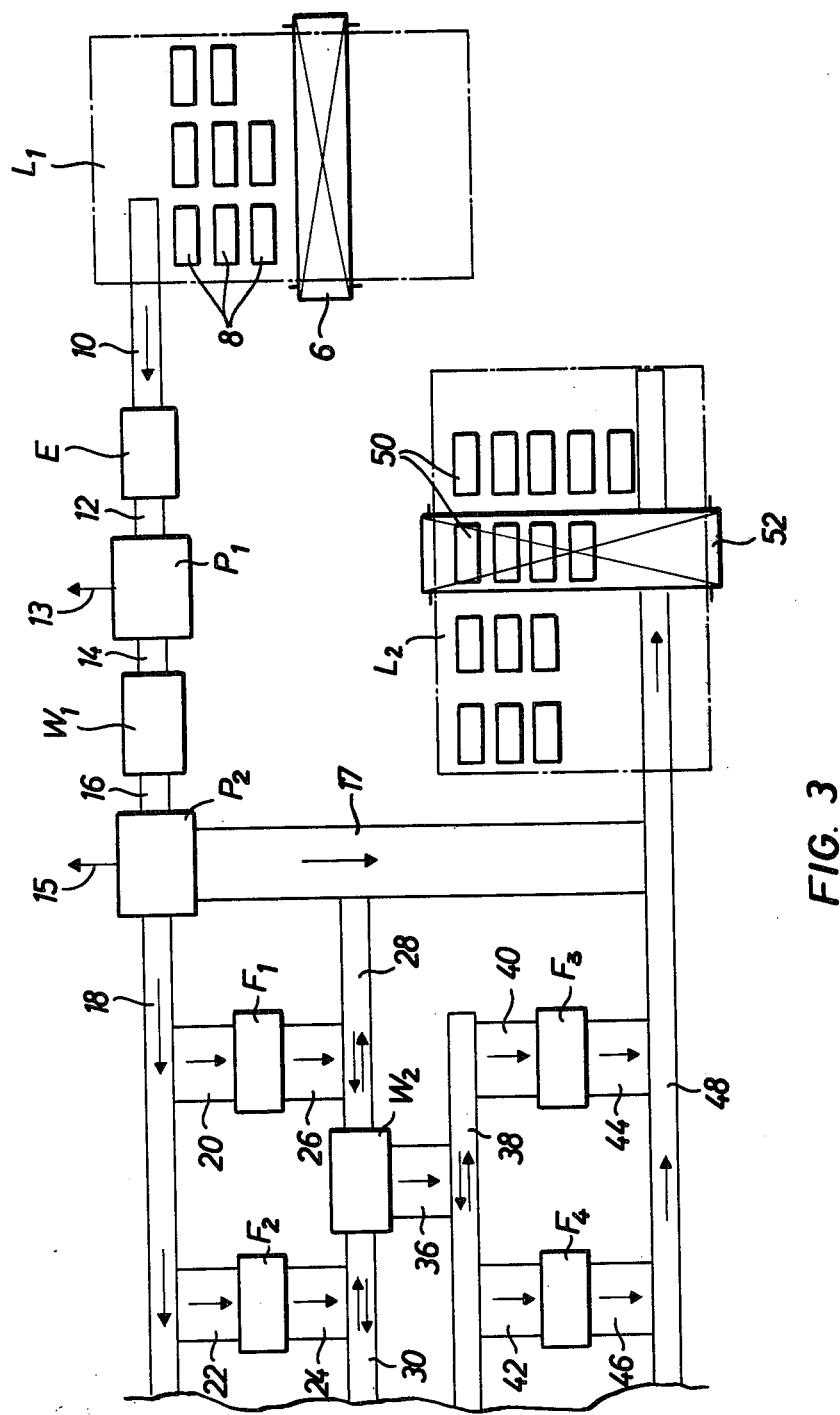
FIG. 3 is a schematic illustration of an operational system for detecting and removing defects.

In FIG. 3, by means of a magnetic crane 6 slabs disposed in stacks 8 on a storage area $L_1$ can be brought onto a roller conveyor 10 and after passing through a descaling apparatus E fed via a roller conveyor 12 to a first inspecting means $P_1$. Here, one of the flat sides of a slab is inspected in that the slab is brought to bear with an end side and a longitudinal side on two stop strips disposed at right angles to each other and the upper flat side is scanned by means of the inspecting means in strips extending in the transverse direction and the defects detected are recorded on a data storage means in the manner described at the beginning. If a slab comprises in the region of its upper flat side one or more defects whose depth is greater than the predetermined value $T_s$ it is separated out at 13 as scrap. Via a roller section 14, a turning means $W_1$ and a rolling section 16 the slabs are fed to the inspecting means $P_2$ by which the second flat side is scanned in analogous manner after arresting the slab in engagement with two stop strips arranged perpendicularly to each other. Slabs found to be scrap are separated at 15 whereas slabs which have no surface defects or only small ones having a maximum depth of $T_1$ are supplied via a roller conveyor 17 and 18 to a storage area $L_2$. By means of roller conveyors 18 and 20 or 22 the slabs to be worked are fed to working means $F_1$ and $F_2$ for the machining of the first flat side and via roller conveyors 24, 30 or 26, 28 to a turning means $W_2$ and roller conveyors 36, 38 and 40 or 42 to two further working means $F_3$ and $F_4$ for working the second flat side. Slabs of which only the first flat side has defects may be brought via roller sections 28, 17 and 48 to the storage area $L_2$. From the working means $F_3$ and $F_4$ the finished slabs may be conveyed via roller conveyors 44, 46 and 48 to the storage area $R_2$ and there stacked to stacks 50 by means of a magnetic crane 52.

As indicated in FIG. 3 the arrangement of roller conveyors, working means and turning means may be analogously extended to the left if further working means are necessary.

It may also be advantageous to make the support arm for the inspecting heads equal to the maximum slab length and to arrange the inspecting heads at intervals of 1, 2, 3 or 4 coordinate units on the support arm and then to scan the slab surface transversely by means of the support arm and after each movement across the slabs surface displace the support arm by one coordinate unit until the surface has been completely scanned.

The use of a scarfing machine has been found particularly advantageous according to the invention, in particular when the depth classification is chosen so that $T_2$ is equal to the working depth on going over a surface portion once and $T_3$ is equal to the working depth on going over the same surface portion twice.

What is claimed is:

1. A method for producing metal blanks, in particular steel slabs, which at least in a predetermined surface area have substantially no defects therein, at least the surface portion to be made free of defects being systematically and substantially completely scanned by at least one inspecting means through relative movement between the inspecting means and the slab surface for detecting defects and for recording their position on the slab surface, and a working means movable relative to the slab surface being controlled in response to the recorded defects, which removes the defects detected, characterized in the steps of dividing the at least predetermined surface area of the steel slab to be inspected into coordinate sub-areas of a two-dimensional coordinate system, determining the positioning of the coordinate sub-areas relative to the slab surface for each individual slab by marks on the steel slab, scanning with the at least one inspecting means the predetermined surface area of the steel slab along at least one coordinate direction of the two-dimensional coordinate system and detecting visible and invisible defects at and closely beneath the predetermined surface of the slab as regards location and depth for each coordinate sub-area, determining and storing the maximum depth to which the defect extends from the surface into the material of the slab for each sub-area, controlling at least one of the working depth and the type of working of at least one working means operable separately and independently from the inspecting means in accordance with the coordinate sub-areas of the two-dimensional coordinate system determined with respect to its position relative to the steel slab by the marks on the steel slab and in accordance with the maximum defect depth stored for the particular surface sub-area to be worked, and positioning the slab in at least one of the inspecting and working positions by contacting a front and longitudinal side surface of the slab with stop means arranged at substantially a right angle to one another.

2. A method according to claim 1, characterized in that the detected defects are divided according to their depth into a plurality of depth classes and storing for each coordinate sub-area only the depth class corresponding to the maximum defect detected for the respective coordinate sub-area.

3. A method according to claim 2, characterized in that the type of working for the at least one slab surface is selected in dependence upon the defect depths stored for the surface.

4. A method according to claim 3, characterized in that the type of working for the at least one slab surface is selected in dependence upon the number of defects stored in the individual depth classes for the surface of the slab.

5. A method according to claim 1, characterized in that when a defect of a slab is stored whose depth exceeds a predetermined maximum depth, the particular slab is separated out as scrap without further processing.

6. A method according to claim 5, characterized in that slabs having no stored defects with depths exceeding a predetermined reference depth are separated out as faultless.

7. A method according to claim 6, characterized in that one surface of the slab is first scanned by the inspecting means and thereafter the slab is turned and another surface of the slab is scanned by one of the same and another inspecting means.

8. A method according to claim 7, characterized in that after inspection of both sides of the slabs, the slabs classified as faultless and the slabs classified as scrap are separated out.

9. A method according to claim 8, characterized in that slabs to be worked are distributed to a plurality of working means carrying out one of the same type and different types of working.

10. A method according to claim 9, characterized in that at least one of the working means is connected via a slab turning means to another working means.

11. A method according to claim 1, characterized in that the at least one inspecting means which detects the particular defect depth and which supplies a result substantially independent of the movement or scanning direction relative to a longitudinal extent of a defect is scanned along the slab surface in a strip manner with a strip width corresponding to the inspecting width of the inspecting means such that the strips substantially completely cover the slab surface substantially without gaps or overlapping at least with their edge regions.

12. A method according to claim 11, characterized in that the slab surface is scanned in parallel strips transversely of the rolling direction of the slab.

13. A method according to claim 1, characterized in that the at least one inspecting means which detects the defect depth and which supplies a result dependent on the movement or scanning direction thereof relatively to a longitudinal extent of a defect scans the slab surface in a strip manner with a strip width corresponding to the inspecting width of the inspecting means in two groups of strips intersecting each other at an angle of 90° such that the strips of each group substantially cover the slab surface substantially without gaps or overlapping at their edges.

14. A method according to claim 1, characterized in that the defects stored by location and depth are stored on a data carrier and the working means is controlled in response to the data carrier.

15. A method according to claim 1, characterized in that at least one of the zero point and direction of the two-dimensional coordinate system correspond with marks of the slabs.

16. A method according to claim 1, characterized in that at least one of individual coordinate lines of the coordinate system and the zero point of the coordinate system is marked on the slab.

17. A method according to claim 16, characterized in that defects are marked on the slab.

18. A method according to claim 1, characterized in that a rectangular X-Y coordinate system is utilized as the two-dimensional coordinate system.

19. A method according to claim 18, characterized in that the X-Y coordinate system is disposed parallel to the longitudinal and transverse direction of the slab with the zero point being in a corner of each of the flat sides of the slab surface to be inspected.

20. A method according to claim 1, characterized in that the width of the coordinate sub-areas of the two-dimensional coordinate system is selected to be substantially no greater than the scanning width of an inspecting means.

21. A method according to claim 1, characterized in that the working width of a working means is selected to be one of equal to and equal to a multiple of the scanning width of an inspecting means.

22. A method according to claim 1, characterized in that the length of the individual coordinate sub-areas are selected to be substantially no greater than the width of the individual coordinate sub-areas.

23. A method according to claim 1, characterized in that at least the predetermined surface area to be inspected is scanned in a strip manner by inspecting heads of at least one inspecting means, the inspecting heads being disposed on a support arm, the distance between the scanned strips of two adjacent inspecting heads being one of equal to a strip width and equal to an integral multiple of a strip width.

24. A method according to claim 23, characterized in that the support arm is displaced with the inspecting means perpendicularly to the strips by an integral number of strip widths and then is scanned in one of the same and opposite directions until there are no unscanned fields between the scanned strips.

25. A method according to claim 23, characterized in that the length of the holding arm before the inspecting heads is made equal only to a fraction of the maximum possible extent of the slab surface to be inspected in the direction of the support arm and after the complete scanning of the support arm width of the slab surface, the support arm with the inspecting heads is displaced substantially by the support arm length in the direction of the support arm to inspect the adjacent slab surface area in the same manner as the first area was inspected.

26. A method according to claim 1, characterized in that each inspecting means is individually mounted in such a manner that on scanning the slab surface each inspecting means remains one of constantly in engagement on the slab surface and a constant distance from the surface, and moves exactly in the scanning direction without actual displacement or deviation.

27. A method according to claim 26, characterized in that the inspecting heads of the inspecting means are mounted movably in a direction perpendicular to the slab surface and are biased against the slab surface with a predetermined force.

28. A method according to claim 1, characterized in that at least one of the inspecting means and working means is disposed on a base support which moves with the slab to be inspected, and that the inspecting means and the working means are led in a manner similar to the case of a stationary slab over the slab surface.

29. A method for producing metal blanks, in particular steel slabs, which at least in a predetermined surface area have substantially no defects therein, at least the surface portion being made free of defects being systematically and substantially completely scanned by at least one inspecting means through relative movement between the inspecting means and the slab surface for detecting defects and for recording their position on the slab surface, and a working means movable relative to the slab surface being controlled in response to the recorded defects, which removes the defects detected, characterized in the steps of dividing the at least predetermined surface area of the steel slab to be inspected into coordinate sub-areas of a two-dimensional coordinate system, determining the positioning of the coordinate sub-areas relative to the slab surface for each individual slab by marks on the steel slab, scanning with the at least one inspecting means the predetermined surface area of the steel slab along at least one coordinate direction of the two-dimensional coordinate system and detecting visible and invisible defects at and closely beneath the predetermined surface of the slab as regards location and depth for each coordinate sub-area, determining and storing the maximum depth to which the defect extends from the surface into the material of the slab for each sub-area, delivering the slab to the area of the working means positioned away from the inspecting means and outside of the path of movement of one of the inspecting means and the slab in relation to the inspecting means, determining the positioning of the two-dimensional coordinate system to enable utilization of the two-dimensional coordinate system by the inspecting means and the working means, and controlling at least one of the working depth and the type of working of at least one working means operable separately and independently from the inspecting means in accordance with the coordinate sub-areas of the two-dimensional coordinate system determined with respect to its position relative to the steel slab by the marks on the steel slab and in accordance with the maximum defect depth stored for the particular surface sub-area to be worked.

30. A method according to claim 29, characterized by positioning the slab in at least one of the inspecting and working positions by contacting a front and longitudinal side surface of the slab with stop means arranged at substantially a right angle to one another.

31. An apparatus for producing metal blanks, in particular steel slabs, having substantially no defects, characterized in that at least one inspecting means for detecting visible and invisible defects in the slab surface is movable over the surface area of the slab at least in one coordinate direction of a two-dimensional coordinate system positioned with respect to the slab surface, the inspecting means detecting the defects and irregularities at and closely beneath the slab surface and the maximum depth which the defect extends from the surface into the material of the slab for coordinate sub-areas of the slab determined by the two-dimensional coordinate system, the coordinate sub-areas being approximately equal in width to the scanning width of an inspecting means, storage means for storing the maximum depth for at least a predetermined period, and at least one working means operable separately and independently from the inspecting means, the working means utilizing the two-dimensional coordinate system and having a working width corresponding to the width of the coordinate sub-areas for which the maximum defect depth is stored, the working depth of the working means being controllable in accordance with the stored maximum defect depths for the coordinate sub-areas, and stop means being arranged at substantially a right angle to one another for contacting a front and longitudinal side portion of the slab for positioning the slab in at least one of the inspecting and working positions.

32. An apparatus according to claim 31, characterized in that a plurality of working means for performing different types of work are provided, each of the working means being operable separately and independently of the inspecting means.

33. An apparatus according to claim 31, characterized in that the inspecting means detects the maximum defect depth classified in at least two depth classes, and the storage means stores the maximum depth class for each coordinate sub-area.

34. An apparatus according to claim 33, wherein the inspecting means is an eddy-current inspecting means.

35. An apparatus according to claim 31, characterized in that the working means is a scarfing means whose working depth is adjustable corresponding to the maximum defect depth determined for the individual surface sub-areas or the depth determined.

36. An apparatus according to claim 31, characterized in that computing means are provided for optimizing the necessary travel of the working means over the slab surface for removing all the defects determined.

37. An apparatus according to claim 31, characterized in that the working means is a scarfing machine and the first defect class to be removed is selected so that its maximum defect depth is equal to the working depth on moving over a surface area once, and the further defect classes are chosen so that they correspond to the working depth of the scarfing machine on moving over the same surface area multiple times.

38. An apparatus according to claim 31, characterized in that the working means is positioned away from the inspecting means and outside of the longitudinal path of one of the inspecting means and the slab in relation to the inspecting means, and means for determining the positioning of the two-dimensional coordinate system to enable utilization of the two-dimensional coordinate system by the inspecting means and the working means.

39. An apparatus for producing metal blanks, in particular steel slabs, having substantially no defects, characterized in that at least one inspecting means for detecting visible and invisible defects in the slab surface is movable over the surface area of the slab at least in one coordinate direction of a two-dimensional coordinate system positioned with respect to the slab surface, the inspecting means detecting the defects and irregularities at and closely beneath the slab surface and the maximum depth which the defect extends from the surface into the material of the slab for coordinate sub-areas of the slab determined by the two-dimensional coordinate system, the coordinate sub-areas being approximately equal in width to the scanning width of an inspecting means, storage means for storing the maximum depth for at least a predetermined period, and at least one working means operable separately and independently from the inspecting means, the working means being positioned away from the inspecting means and outside of the path of movement of one of the inspecting means and the slab in relation to the inspecting means, the working means utilizing the two-dimensional coordinate system and having a working width corresponding to the width of the coordinate sub-areas for which the maximum defect depth is stored, the working depth of the working means being controllable in accordance with the stored maximum defect depths for the coordinate sub-areas, and means for determining the positioning of the two-dimensional coordinate system to enable utilization of the two-dimensional coordinate system by the inspecting means and the working means.

* * * * *